United States Patent [19]

Moser

[11] Patent Number: Plant 7,378

[45] Date of Patent: Nov. 13, 1990

[54] HIBISCUS PLANT NAMED ISLAND FIRE

[75] Inventor: Frank C. Moser, Alva, Fla.

[73] Assignee: Yoder Brothers, Inc., Barberton, Ohio

[21] Appl. No.: 397,176

[22] Filed: Aug. 21, 1989

[51] Int. Cl.[5] ..... A01H 5/00

[52] U.S. Cl. ..... Plt./54

[58] Field of Search ..... Plt. 54

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Hibiscus plant named Island Fire particularly characterized by its bright red flower color with a dark red eye, regular flower form with slightly reflexed flowers, dark green medium sized leaves with a serrated edge, excellent pot habit, flower life of a single day, excellent bud drop resistance, ease of propagation, and excellent resistance to bacterial leaf spot.

2 Drawing Sheets

The present invention comprises a new and distinct cultivar of hibiscus, botanically known as *Hibiscus Rosa-sinensis L.*, and referred to by the cultivar name Island Fire.

Island Fire, identified as 83-047-001 during the breeding and selection process, originated from a planned cross hybridization between two selected breeding lines in a controlled breeding program in Fort Myers, Fl. by Frank C. Moser.

The female, or seed parent is a breeding line designated as code #0001 and the pollen, or male parent is a breeding line designated as code #0002.

Island Fire was discovered and selected as a flowering plant within the progeny of the stated cross by Fank C. Moser in July, 1983, outside in ground beds in Fort Myers, Fl.

The first asexual reproduction of Island Fire was accomplished when vegetative cuttings were taken from the initial plant selection in October, 1983 in Fort Myers, Fl. from plants grown outside in ground beds, by technicians working under formulations established and superivsed by Frank C. Moser.

Horticultural examinations of controlled flowerings of successive generations of plants derived from cuttings taken from the original selection have shown that the unique combination of characteristics as herein disclosed for Island Fire are fixed and retained through successive generations of asexual reproduction Island Fire has not been observed under all possible environmental conditions. The phenotype may vary significantly with variations in environment such as temperature and light intensity.

The following observations, measurements and comparisons described plants that were grown in Fort Myers, Fl. in a controlled greenhouse environment and following a commercial schedule.

The following traits have been repeatedly observed and are determined to be basic characteristics of Island Fire, which, in combination, distinguish this Hibiscus as a new and distinct cultivar:

1. Bright red flower color with a dark red eye.
2. Regular flower from with slightly reflexed flowers.
3. Medium sized leaves, dark green, with a serrated edge.
4. Excellent pot habit.
5. Flower life, a single day.

6. Excellent bud drop resistance.
7. Easy to propagate.
8. Excellent resistance to bacterial leaf spot.

The accompanying photographic drawings show typical habit, flower and leaf characteristics of Island Fire, with colors being as nearly true as possible with illustrations of this type.

Sheet 1 is a color photograph of Island Fire grown as a commercially finished pot plant.

Sheet 2 is a black and white photograph showing the variation in leaf shape that can characteristically be found on any one plant of Island Fire.

Of the commercial cultivars known to the inventor, the most similar in comparison to Island Fire is the cultivar Brilliant Red.

Island Fire is similar to Brilliant Red in that both cultivars produce bright red flowers with a dark red eye. Both cultivars have cigar shaped buds and both have entire leaves with a serrated margin. Island Fire and Brilliant Red both produce flowers which reflex their petals.

Island Fire differs from Brilliant Red in that the flowers are slightly darker, while the eye is not as intense. Island Fire has a much better pot habit, is much easier to root, is bud drop resistant and much less sensitive to bacterial leaf spot than Brilliant Red. The stigma branches are half the length of those found on Brilliant Red. The leaf shape of Island Fire is ovate-lanceolate with a slight serrated margin while the leaf shape of Brilliant Red is ovate with a deep serration. The flowers of Island Fire are smaller than those of Brilliant Red.

In the following description, color references are made to The Royal Horticultural Society Color Chart. The color readings were taken from greenhouse grown plants on Mar. 5, 1989. All readings were taken in an office under cool white fluorescent lights, facing a west window between the hours of 10:00 A.M. and 2:00 P.M.

Classification:

*Botanical.*—*Hibiscus Rosa-sinensis* L. cv. Island Fire.

*Commercial.*—Greenhouse pot crop.

Inflorescence

A. Flower (general):

*Size.*—13.0 cm.

*Borne.*—In axils of leaves, 1 per node.
*Form.*—Regular single, sometimes reflexing its petals
*Life.*—1 day.
*Fragrance.*—None.
*Blooming habit.*—Continuously, year round.

B. Corolla (petals):
*Texture.*—Smooth, veins slightly raised up.
*Substance.*—Medium thick.
*Shape.*—Rounded
*Color (fully open).*—Eye: Red 46A. Throat: None. Zone: None. Body: Red 44A, vines red 44A. Edge: None.

C. Bud (one day prior to opening):
*Size.*—6.5 cm.
*Shape.*—Cigar shaped.
*Color.*—Red 45B.

D. Calyx: Cup shaped, 5 pointed lobes, a single prominent midvein per lobe, membranous
*Length.*—4.0 cm.
*Color.*—Green 144A.

E. Epicalyx:
6–8 pointed, narrow, sword-shaped bracts.
*Length.*—1.0–1.7 cm.
*Color.*—Green 141A.

F. Peduncle:
*Length.*—4.5–5.0 cm.
*Strength.*—Strong.
*Aspect.*—Smooth.
*Color.*—Above the abscission layer, green 143A, at and below the abscission layer green 143 interspersed with red 53A.

G. Reproductive organs:
1. *Androecium (stamens).*—Anthers: Numerous. Filaments: Length 1.0 cm. Pollen: Abundant. Color: Yellow 15A. Staminal column: Upper 30% antheriferous Length: 8.5 cm. Color: Red 44B.
2. *Gynoecium (pistil).*—Stigma: 5 in number, rounded, discoid, hairy. Diameter: 3.0 mm. Color: Red 46A. Style: Length: 9.2 cm. Color: Yellow 2D. Branches: 5 in number. Color: Red 44A. Length: 0.7 cm. Ovary: Bell shaped. Color: Yellow Green 154C.

PLANT CHARACTERISTICS

A. Foliage:
*Arrangement.*—Alternate.
*Shape.*—Juvenile: Ovate/lanceolate. Mature: Ovate/lanceolate. Color: Dark green 139A.
*Petiole.*—Length: 3.5–4.0 cm. Aspect: Smooth. Color: Dark green 147A.
*Stipules.*—Two per node, shape acicular (needle shaped). Color: Green 147A.

B. Stem: Aspect smooth, becoming woody with age.
C. Plant habit: Excellent.
D. Breaking action: Excellent.
E. Rooting: Excellent.
F. Growth regulator: Required.
G. Low light bud initiation: Good.
H. Shipping tolerance: Excellent.

I claim:

1. A new and distinct cultivar of Hibiscus plant named Island Fire, as described and illustrated.

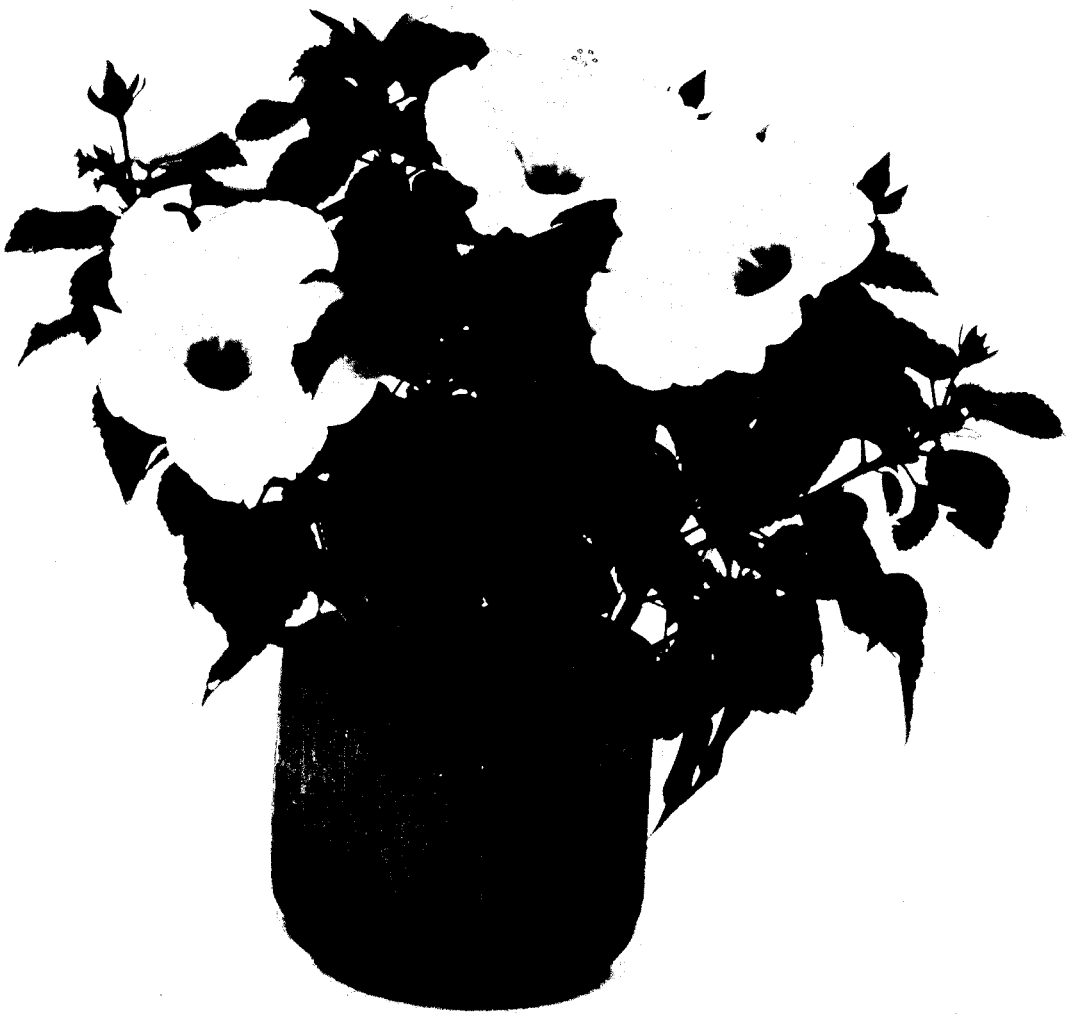

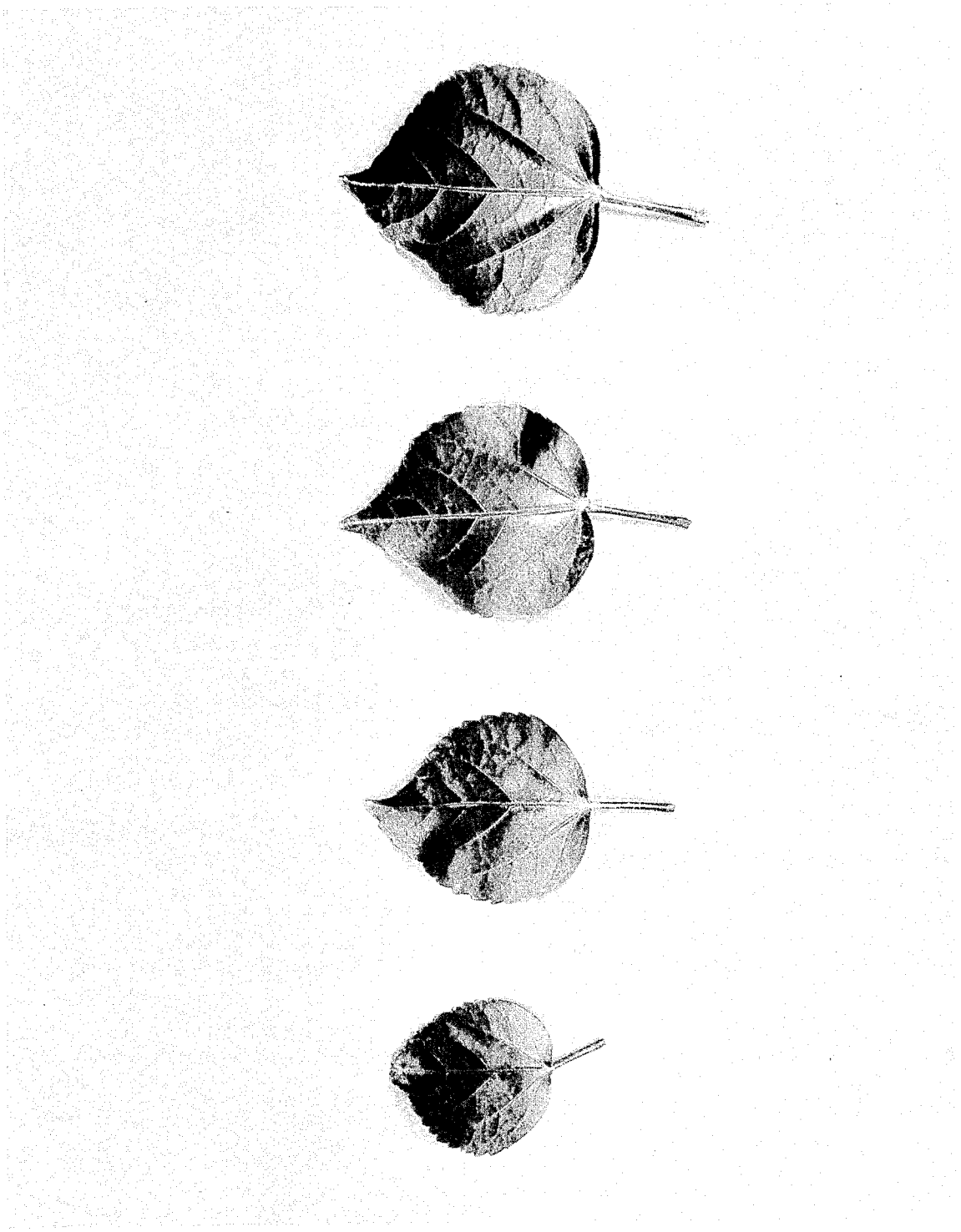

* * * * *